United States Patent [19]

Cannelongo

[11] Patent Number: 4,674,445

[45] Date of Patent: Jun. 23, 1987

[54] DEVICE AND METHOD FOR CONTROLLING INSECTS

[75] Inventor: Joseph F. Cannelongo, Piscataway, N.J.

[73] Assignee: American Cyanamid Company, Stamford, Conn.

[21] Appl. No.: 760,216

[22] Filed: Jul. 29, 1985

[51] Int. Cl.[4] ............................................. A01K 13/00
[52] U.S. Cl. ...................................... 119/156; 40/301
[58] Field of Search .......................... 119/156; 40/301

[56] References Cited

U.S. PATENT DOCUMENTS

| | | | |
|---|---|---|---|
| 3,318,679 | 5/1967 | Smith et al. | 71/2.5 |
| 3,731,414 | 5/1973 | Murphy et al. | 40/301 |
| 3,756,200 | 9/1973 | Ohlhausen | 119/156 |
| 3,942,480 | 3/1976 | Hair et al. | 119/156 |
| 3,944,662 | 3/1976 | Miller, Jr. et al. | 424/78 |
| 4,059,074 | 11/1977 | Furer et al. | 119/156 |
| 4,195,075 | 3/1980 | Miller | 424/14 |
| 4,579,085 | 4/1986 | McGuire | 119/156 |

Primary Examiner—Robert P. Swiatek
Assistant Examiner—Hugh R. Chamblee
Attorney, Agent, or Firm—Alice C. Brennan

[57] ABSTRACT

The present invention relates to novel insecticidal animal ear tags and a method for controlling insects.

13 Claims, 8 Drawing Figures

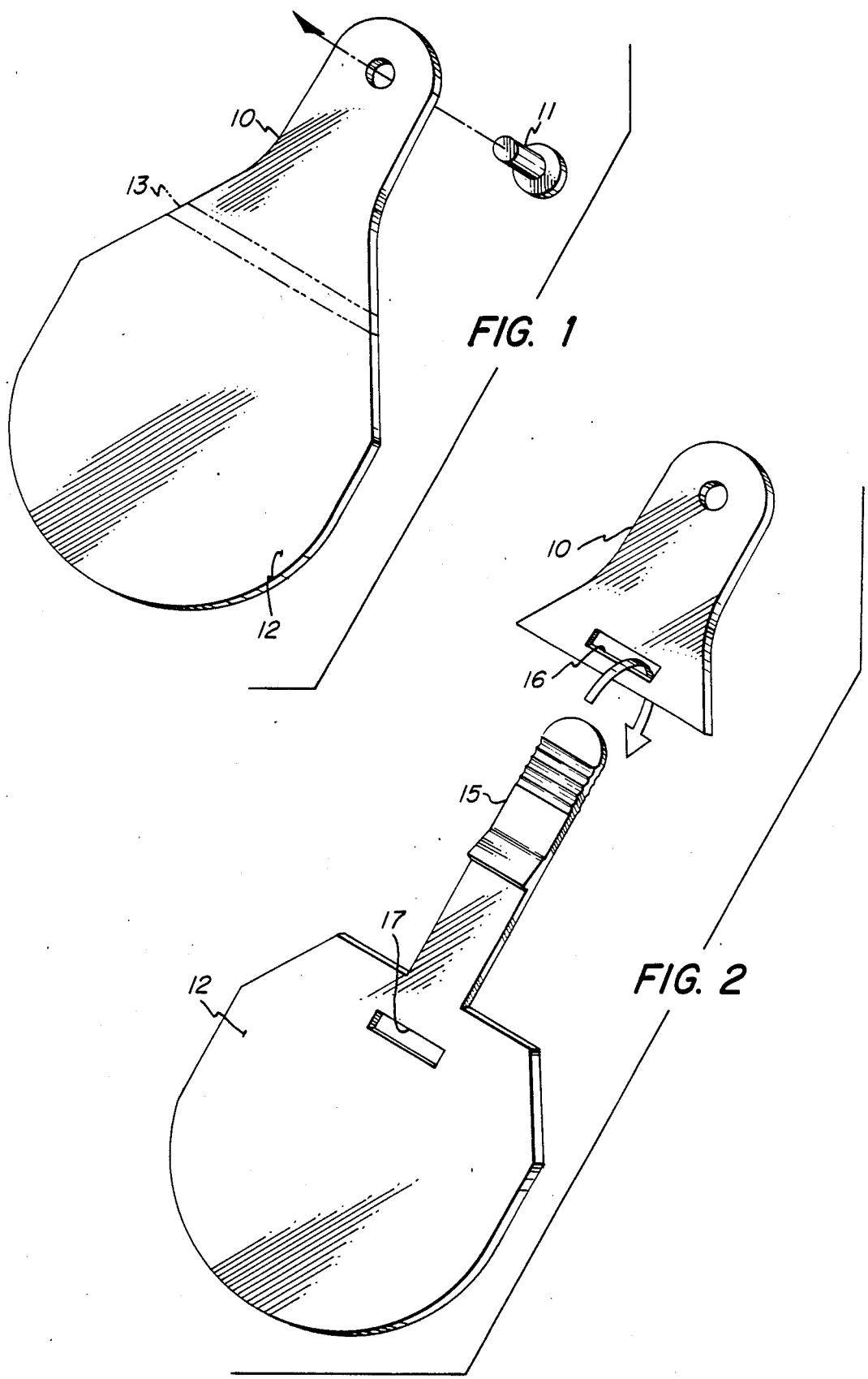

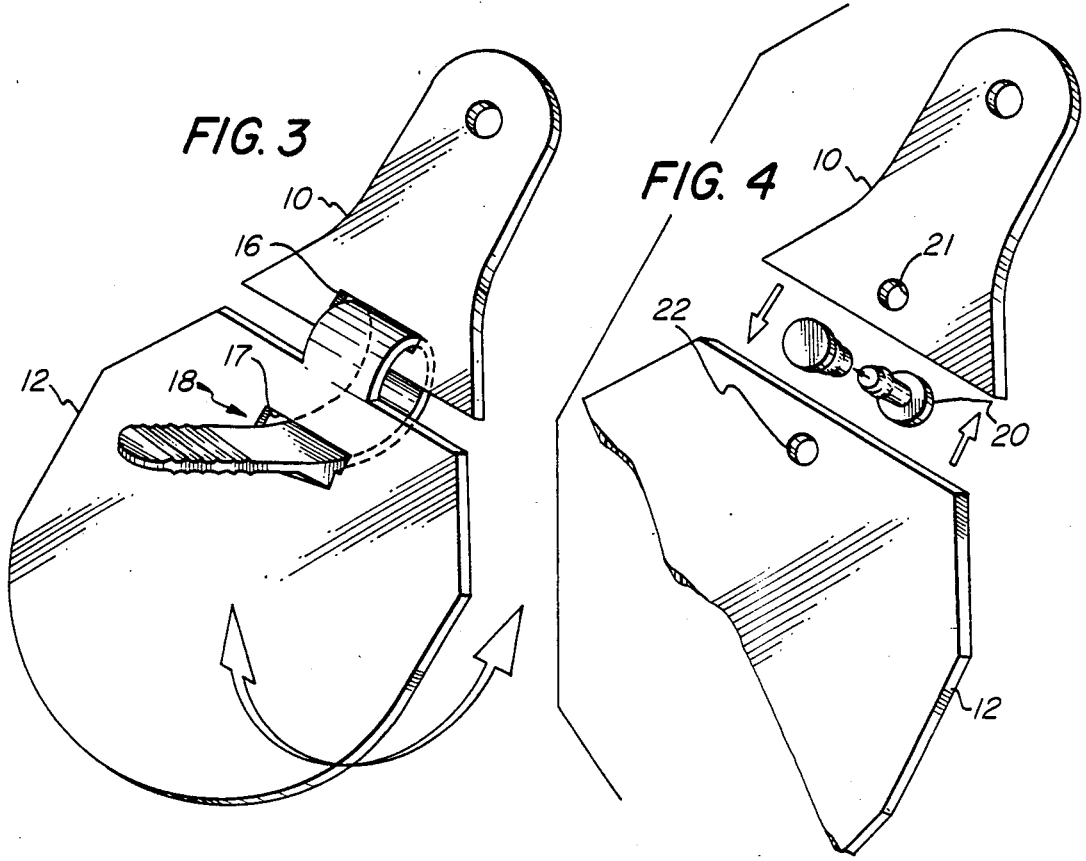
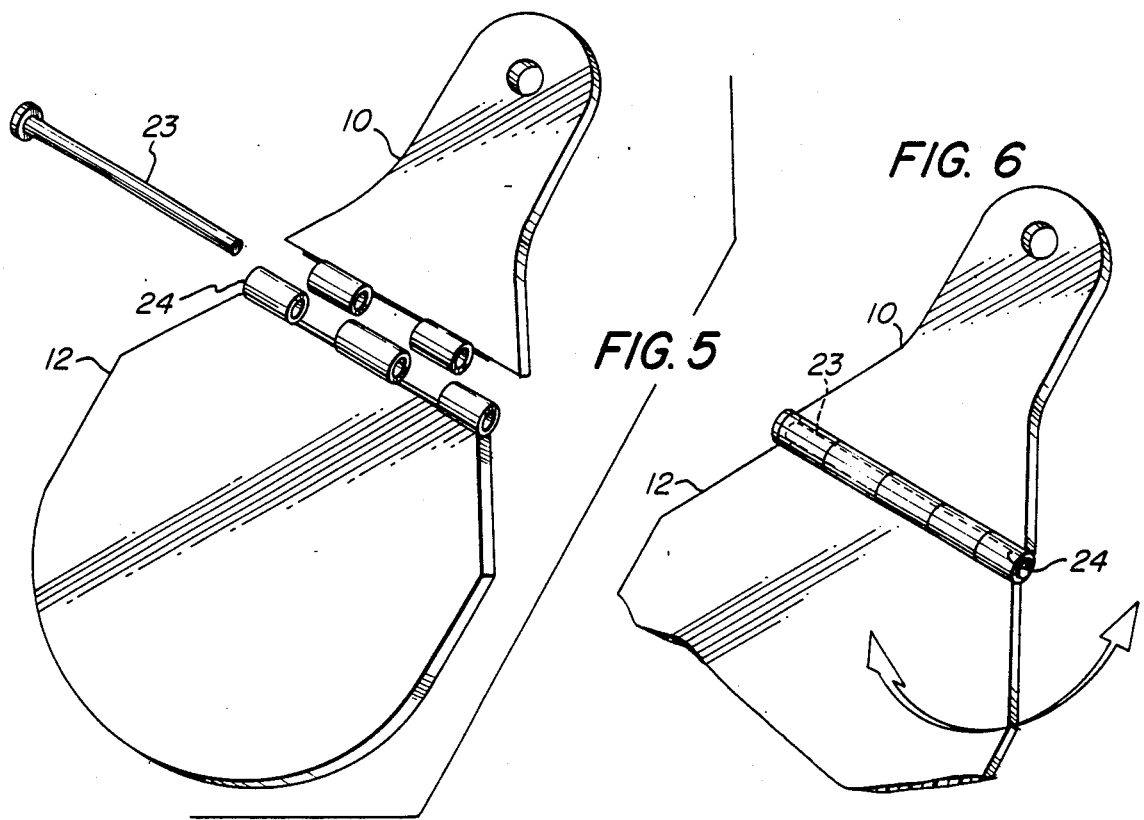

DEVICE AND METHOD FOR CONTROLLING INSECTS

BACKGROUND OF THE INVENTION

The present invention relates to a device and method for controlling insects. Many recently developed techniques used for the control of insects involve slow-release pesticide technology. The use of pest strips, collars, bands, and tags which have an insecticide contained throughout the substrate of the final device are described in U.S. Pat. No. 3,318,679; U.S. Pat. No. 3,944,662; U.S. Pat. No. 3,756,200; U.S. Pat. No. 3,942,480 and U.S. Pat. No. 4,195,075. The latter patent describes an insect control device containing an insecticidally-active isomer of $\alpha$-cyano-3-phenoxy-benzyl-$\alpha$-isopropyl-4-chlorophenylacetate. Application for U.S. Ser. No. 615,611, filed May 31, 1984, describes coated devices which enable the incorporation of insecticidal agents which were not suitable for incorporation into devices prepared by extrusion and injection molding.

The increased popularity of devices such as insecticidal animal ear tags over the past few years, has resulted in considerable effort to develop improved devices to overcome the problems which become apparent as their use increases. Improvements in design, compositions, and manufacturing techniques are constantly being sought to overcome problems such as breakage and loss, and to improve efficacy and ease of application. Breakage and loss occur in ear tags such as those described in U.S. Pat. No. 3,731,414, due to their size, design and method of attachment which results in portions of the tag being subjected to flex and stress in the field for prolonged periods of time. Additionally, breakage or weakness of a plastic tag can result from the incorporation of an active ingredient or mixture of active ingredients which may actually weaken the polymer matrix.

Interference of an active component with the polymerization or manufacturing process, resulting in weakness and breakage, is an area of great concern in the preparation of animal ear tags. An increasing emphasis is being placed on combinations of insecticidal ingredients, such as the pyrethroids with other insecticides, and the use of synergists, such as piperonyl butoxide, in order to increase the efficacy and spectrum of activity of insecticidal animal ear tags. Increases in the concentrations of active component is currently limited by the strength of the resulting plastic tag.

It is an object of this invention to provide compositions and devices which are not restricted by the above limitations.

SUMMARY OF THE INVENTION

The invention relates to an animal ear tag comprising a first component capable of being attached to the ear of an animal, a second component containing an insecticidally active ingredient or mixture of insecticidally active ingredients, and a means for connecting the two components, wherein the components are joined together to provide for a degree of motion between the first and second components.

The two component ear tags of the invention not only control insects but also overcome certain problems associated with conventional insecticidal ear tags. The ear tags of the invention can better withstand the flex and stress pressures present in the field over prolonged periods of time, thereby resulting in reduced ear tag breakage and loss. The novel, stronger ear tags are capable of holding a high concentration and/or different types of insecticides, thereby increasing their efficacy and spectrum of activity. An additional advantage of the animal ear tags of this invention is that the second component may be replaced without having to repuncture the ear of the animal each time the insecticide needs replacing.

BRIEF DESCRIPTION OF THE DRAWINGS

FIG. 1 shows an ear tag according to an embodiment of the invention.

FIG. 2 shows a first component having an opening and second component having an integrated strap.

FIG. 3 shows first and second components fastened together and the degree of motion between the components.

FIG. 4 shows first and second components to be fastened by a removable pin.

FIG. 5 shows hinge components attached to the first and second components.

FIG. 6 shows the first and second components hinged together.

PREFERRED EMBODIMENT OF THE INVENTION

Referring to FIG. 1 of the drawings, the first component 10 is attached to an animal's ear using pin 11. The second component 12 which contains the insecticidally active ingredient(s) is joined to the first component by connecting means 13.

Figure 7:
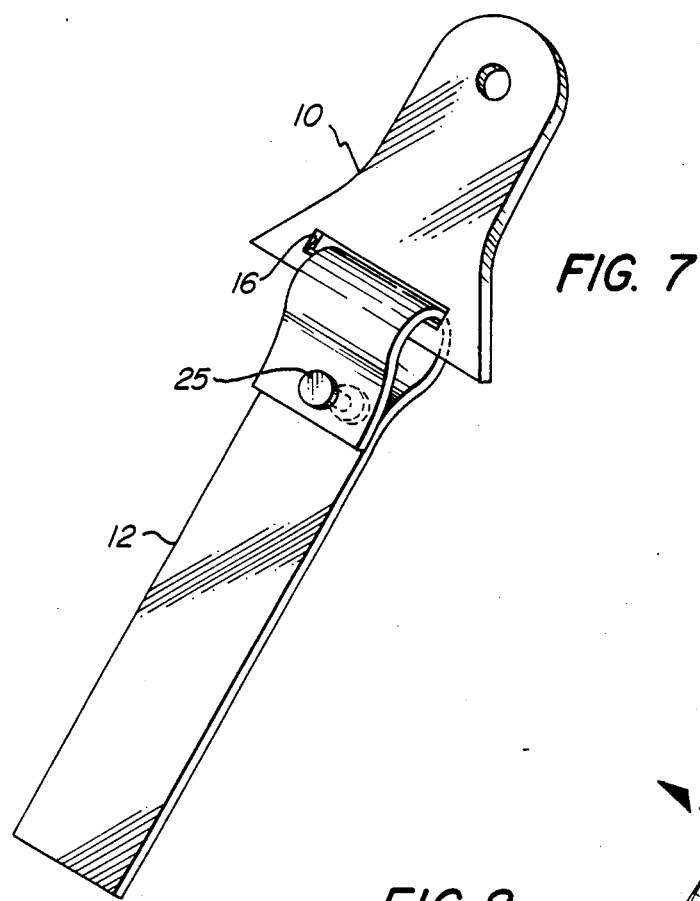
FIG. 7 shows first and second components joined by passing a pin through the second component.

The connecting means 13 schematically illustrates any assembly which allows a degree of motion between the first and second components of the ear tag. The assembly may be integrated into the first and/or second components. Alternately, the assembly may employ independent straps, wires, pins, clips, hinges and bushing means. Referring to FIGS. 2 and 3 of the drawings, the connecting means may be integrated strap 15 which when inserted through opening 16 of first component 10 and through opening 17 of second component 12 forms hinged assembly 18. In FIG. 4, the first and second components are to be removably joined by passing pin 20 through opening 21 and 22. FIGS. 5 and 6 show first and second components hinged together by inserting removable pin 23 through the hinge components 24 attached to the first and second components. FIG. 7 shows the second component 12 passing through opening 16 of first component 10 whereupon the second component is joined to itself by pin 25.

The first component of the invention may be constructed of virtually any material of suitable size and strength. Preferably the first component is manufactured from thermoplastics, such as polyvinylchloride resins and polyurethane elastomers.

A suitable pin for the invention may be of any design including that of a bayonet type system, provided it pierces the ear of an animal and holds the ear tag in place. A means for securing the pin may optionally be employed and it may be either an integral part of the design or an independent unit. U.S. Pat. No. 3,731,414, which is herein incorporated by reference, discloses a preferred means of attachment to the animal's ear which is suitable for the present invention.

The insecticidal bearing second component is normally comprised on a weight basis of about 44.0% to 71% of a polyvinylchloride or other thermoplastic; about. 0.0% to 4.0% of a processing stabilizer such as epoxidized soybean oil; about 0.2% to 10.0% of a lubricant such as stearic acid; about 0.3% to 0.5% of a chelating agent such as trinonylphosphite; about 1% to 2.5% of a heat processing stabilizer such as calcium-zinc stearate; about 0% to 5.0% of a flow agent such as $SiO_2$; about 0% to 35.0% of insecticidal synergists and migration accelerators such as piperonyl butoxide; about 5.0% to 25.0% of a plasticizer or mixture of plasticizers such as dioctylphthalate, benzylbutylphthalate, dibutylphthalate, citrate esters, adipates or sebacates; about 1% to 30% of insecticide or mixture of insecticides, such as pyrethroids, organophosphates, or carbamates.

The generic names and the corresponding chemical names of the preferred insecticides and synergists for use in the invention include those listed below and mixtures thereof.

TABLE I

| Generic Name | Chemical Name |
|---|---|
| Flucythrinate | ($\pm$)-cyano(3-phenoxyphenyl)methyl ($\pm$)-4-(difluoromethoxy-$\alpha$-(1-methylethyl)benzeneacetate |
| Cypothrin | Cyano(3-phenoxyphenyl)methyl spiro-[cyclopropane-1,1'-[1H]indene]-2-carboxylic acid |
| Fenvalerate | Cyano(3-phenoxyphenyl)methyl 4-chloroalpha-(1-methylethyl)benzeneacetate |
| Permethrin | 3-(Phenoxyphenyl) methyl ($\pm$)-cistrans-3-(2,2-dichloroethenyl)-2,2-dichloroethenyl)-2,2-dimethyl cyclopropane carboxylate |
| Cypermethrin | $\pm$-Cyano-3-phenoxybenzyl ($\pm$)-cistrans-3-(2,2-dichlorovinyl)-2,2-dimethyl cyclopropane carboxylate |
| Deltamethrin | (S)-$\alpha$-Cyano-m-phenoxybenzyl (1R, 3R)-3-(2,2-dibromovinyl)-2,2-dimethylcyclopropanecarboxylate |
| Resmethrin | ({5-(Phenylmethyl)-3-furanyl} methyl-2,2-dimethyl-3-(2-methyl-1-propenyl)cyclopropanecarboxylate |
| Tetramethrin | 1-cyclohexene-1,2-dicarboximido-methyl-2,2-dimethyl-3-(2-methyl-propenyl)-cyclopropanecarboxylate (3,4,5,6-tetrahydrophthalimido-methyl ($\pm$)-cistrans-chrysan-themate |
| Flumethrin | Cyano(4-fluoro-3-phenoxyphenyl)-methyl 3-[2-chloro-2-(4-chloro-phenyl)ethenyl]-2,2-dimethylcyclo-propanecarboxylate |
| Cyhalothrin | Cyano(3-phenoxyphenyl)methyl 3-(2-chloro-3,3,3-trifluoro-1-pro-penyl)-2,2-dimethylcyclopropane-carboxylate |
| Fluvalinate | Cyano(3-phenoxyphenyl)methyl N—[2-chloro-4-(trifluoromethyl)-phenyl] DL-valinate |
| Dimethoate | 0,0-dimethyl S—(N—methylcarbamoyl-methyl)phosphorodithioate |
| Dibrom | 1,2-Dibromo-2,2-dichloroethyl dimethyl phosphate |
| Chlorfenvinphos | 2-Chloro-1-(2,4-dichlorophenyl)-vinyl diethyl phosphate |

The insecticidal bearing second component may be fabricated out of a material which is preferably different from the material of the first component. This second component may be fabricated on a matrix such as a natural or synthetic cloth or fiber mesh for example, polyaramid or a polyester, wire mesh or a solid matrix by coating, extruding, coextruding or impregnating onto the matrix.

The insecticide containing component may be fabricated by preparing a blend of the dry ingredients by admixing them in a blender, heating the mixture while blending it in a temperature range of 80° to 120° C. and slowly adding a mixture of the liquid ingredients and mixing until a relatively dry blend is obtained. The resulting homogeneous blend is cooled while mixing and $SiO_2$ added and blended in to obtain a homogeneous dry blend, which may then be molded, extruded or coextruded optionally onto a matrix or the dry blend may then be pelletized by extrusion and the pelletized dry blend then molded, extruded, or coextruded optionally onto a matrix as described above and punched or cut into the desired shape. Alternatively, the insecticide containing component may be prepared by coating or dipping a matrix with a vinyl dispersion containing the active ingredients, as disclosed herein by reference to U.S. patent application Ser. No. 615,611, filed May 31, 1984, which is incorporated by reference.

Additionally, this second component may contain more than one section. Individual sections may be composed of the same or different ingredients and may also provide different release rates of active ingredients. Such a second component allows for the application of active ingredients which would not be compatible in a single section as well as an alternative method for delivering mixtures of active ingredients at the same or different rates.

Figure 8:
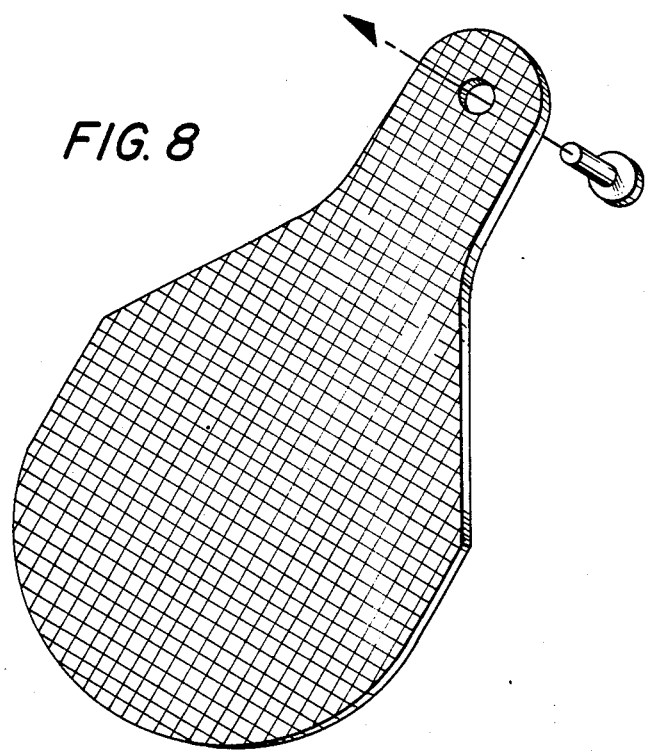
FIG. 8 shows another embodiment of the invention where the ear tag is composed of one plastic coated component which is fabricated on a matrix.

It has also been found that the use of impregnated coated, extruded or coextruded fabric matrix tags of a one piece design offers several advantages over conventional one piece molded tags. When a composition containing an insecticidally active ingredient or mixture of insecticidally active ingredients is fabricated on a matrix of natural or synthetic cloth or fiber mesh, or a wire mesh, the result is a stronger ear tag which is less prone to breakage and thus allows a greater range of compositions to be incorporated into the tag. Also, the one piece matrix animal ear tag, due to the strength of the matrix, is not as restricted in the means of attachment to the ear as a plastic molded ear tag (See FIG. 8).

The invention is further illustrated by the following non-limiting examples. The first or second components shown herein are intended to encompass all design modifications including different shapes and sizes.

EXAMPLE 1

Preparation of an Ear Tag

A. Dry Blend

Dry blends of various compositions are prepared utilizing the ingredients listed in Table II below by blending the solid ingredients until a homogeneous mixture is obtained and then heating the mixture to 85° C. A mixture of the liquid ingredients is then slowly added to the agitated mixture. When all of the liquid is added to the mixture, the mixture is heated to 110° C. and agitated for 10 minutes. The agitated blend is cooled to 70° C. and sufficient $SiO_2$ is added to obtain a free-flowing dry blend. The dry blend is then cooled to ambient temperatures and collected.

TABLE II

| | Parts by Weight | % by Weight |
|---|---|---|
| Polyvinylchloride | 100 | 44.4–62.9 |

TABLE II-continued

| | Parts by Weight | % by Weight |
|---|---|---|
| Epoxidized Soybean Oil | 10.88 | 4.8–6.8 |
| Stearic Acid | 0.54 | 0.2–0.3 |
| Trinonylphosphate | 0.65 | 0.3–0.4 |
| Ca/Zn Stearate | 1.96 | 0.9–1.2 |
| $SiO_2$ | 0.71 | 0.3–0.4 |
| Hyp 212P | 0.44 | 0.2–0.3 |
| Hyp 211P | 0.76 | 0.3–0.4 |
| HW 132P | 1.09 | 0.5–0.7 |
| UV Stabilizer 5411 | 0.65 | 0.3–0.4 |
| Pyrethroid Insecticide | 17.74 to 19.00 | 7.9–12 |
| Kevlar | 0.0 to 5.61 | 0.0–3.5 |
| Piperonylbutoxide | 4.54 to 36.0 | 2.0–22.7 |
| Plasiticers | 18.9 to 46.0 | 8.4–29.5 |
| benzylbutylphthalate | | |
| dibutylphthalate | | |
| dioctylphthalate | | |
| acetyltributyl citrate | | |
| dioctyladipate | | |

B. Pelletizing

The compositions prepared in A above may be pelletized using standard low shear extruders at elevated temperatures normally in the range of 300° F. to 350° F. The resulting extruded material is then cut to the desired size by air chopping and the resulting pellets are packaged.

C. Injection Molding

Pellets prepared as in B above are charged to a 350 ton press and the temperature and time profile is set to 325° F. for twenty seconds. The compositions are molded to the desired size by injection molding or extruded and the resulting components packaged.

D. Extrusion

The pellets or the dry blend prepared as in A or B above may also be fabricated into a tape or extruded or coextruded onto a fabric matrix by passing the melt through a profile die and then cutting to the desired size and shape.

EXAMPLE 2

Effectiveness of the insecticidal components

Insecticidal components are prepared using the dry bends prepared as described in Example 1A, containing 36 parts of weight of piperonylbutoxide, 18 parts by weight of the synthetic pyrethroid, flucythrinate, and 18 parts by weight of several plasticizers per 100 parts of PVC. These dry blends are pelletized and extruded onto a cloth matrix and punch and die cut to the desired shape giving an insecticidal component weighing approximately 8 grams.

These insecticidal components are hung in a chamber covered with mesh cloth to keep the flies confined in the 12"×17"×9" space. Each chamber contains a cup of water and a supply of sugar and powdered milk.

At the start of the test, ~100 three to five day old house flies are placed in each chamber. The chambers are kept in a room with the temperature at 82° F. The flies are observed daily (except Saturday and Sunday) and mortality is recorded. At the termination of the study, the chambers are placed in a freezer overnight to kill the remaining flies, which are counted. The percent mortality is calculated based on the number of flies that die during the observation period and the number of flies counted at the end of the study.

The results of these experiments are summarized in Table III below and demonstrate the effectiveness of the insecticidal component of the present invention.

TABLE III

| PVC | Kevlar | Plasticizer | 7 Day Fly Morality % |
|---|---|---|---|
| 100 | — | DOP | 99 |
| 100 | 5.61 | DOP | 95 |
| 100 | — | BBP | 98 |
| 100 | — | DAP | 74 |

EXAMPLE 3

Preparation of insecticidal coating composition containing a synthetic pyrethroid and organophosphate insecticides Butyl benzyl phthalate 180 g is added to a stirred mixture of 300 g of a vinyl resin having an inherent viscosity of 1.20 and average particle size of 0.95 microns and 6 g of Ca/Zn stearate and 9 g of epoxidized soybean oil. To this stirred mixture is added 44.66 g of dimethoate and 55.83 g of flucythrinate (80% pure). The resulting mixture is stirred until homogeneneous and deaerated at room temperature overnight at 686 mm/Hg.

EXAMPLE 4

Preparation of insecticide containing component of a two piece tag containing a mixture of synthetic pyrethroid and organophosphate insecticides A solid matrix is preheated to 100° C. and dipped into the insecticidal coating composition prepared in Example 2. The resulting coated components are cured in an oven at 90° C. to 135° C. for five to eight minutes, resulting in coated matrixes containing 1.7 g to 2.86 g of the insecticidal coating composition.

EXAMPLE 5

Preparation of coated matrix containing various synthetic pyrethroids alone and in combination with various organophosphate insecticides (a) A vinyl dispersion is prepared utilizing the procedure of Example 3 and the materials listed in Table VI below.

TABLE IV

| Ingredient | Wt g | % Wt of Dispersion |
|---|---|---|
| Resin (Inherent viscosity 1.20 average particle Size 0.95 microns | 300 | 49.72 |
| Butyl benzyl phthalate | 180 | 29.82 |
| Epoxidized soybean oil | 9 | 1.49 |
| Ca/Zn Stearate | 6 | 0.99 |
| Benzophenone ultra violet stablizer | 2 | 0.33 |

(b) Insecticidal combination coating compositions may then be prepared by addition of the insecticidal compositions illustrated in Table V below to the vinyl dispersion prepared in Example 5(a) and blending until homogeneous. The resulting mixture is then deaerated at reduced pressure 686 mm/Hg for 16 hours, giving an insecticidal combination coating composition suitable for preparing coated insect control devices.

(c) Insect control devices may then be prepared by coating and curing the resulting coated matrix at 90° C. to 135° C. for 2-10 minutes.

TALBE V

| Pyrethroid | Dimethoate | Dibrom | Chlorfenvinphos | Vinyl Dispersion of Example 6 |
|---|---|---|---|---|
| Flucythrinate | 7.5/7.5 | 7.5/7.5 | 7.5/7.5 | 85 |
| Fenvalerate | 7.5/7.5 | 7.5/7.5 | 7.5/7.5 | 85 |
| Cypermethrin | 7.5/7.5 | 7.5/7.5 | 7.5/7.5 | 85 |
| Permethrin | 7.5/7.5 | 7.5/7.5 | 7.5/7.5 | 85 |
| Cypothrin | 7.5/7.5 | 7.5/7.5 | 7.5/7.5 | 85 |
| Deltamethrin | 7.5/7.5 | 7.5/7.5 | 7.5/7.5 | 85 |
| Fluvalinate | 7.5/7.5 | 7.5/7.5 | 7.5/7.5 | 85 |
| (Z)-trans-α-cyano-m-phenoxy benzyl 3-(β-cyano-styryl)-2,2-dimethylcyclo-propanecarboxylate | 7.5/7.5 | 7.5/7.5 | 7.5/7.5 | 85 |

EXAMPLE 6

Insecticidal evaluation of coated matrix containing various pyrethroids and organophosphates Combination coated matrixes which are prepared by the procedure of Example 5 are screened for insecticidal effectiveness by suspending each cured coated matrix being evaluated in a one gallon cylindrical container containing 100 three to five day old flies containing a container of aqueous milk and sugar solution. Each composition is tested in replicate against a control. The containers are kept in a room maintained at 82° F. and the percent mortality determined after 24 hours exposure. The results of these experiments which are summarized in Table VI below demonstrate the effectiveness of coated matrixes containing 7.5% by weight of a pyrethroid insecticide and/or 7.5% by weight of an organophosphate insecticide within the coating.

TABLE VI

| Insecticidal Composition | Average % Mortality 24 Hours |
|---|---|
| Flucythrinate 7.5% plus dimethoate 7.5% | 61 78 |
| Flucythrinate 7.5% plus dibrom 7.5% | 97 99 |
| Flucythrinate 7.5% plus chlorfenvinphos 7.5% | 1 0 |
| Fenvalerate 7.5% plus 7.5% dimethpate | 59 74 |
| Fenvalerate 7.5% plus chlorfenvinphos 7.5% | 2 1 |
| Cypermethrin 7.5% plus dimethoate 7.5% | 57 62 |
| Cypermethrin 7.5% plus dibrom 7.5% | 99 99 |
| Cypermethrin 7.5% plus chlorfenvinphos 7.5% | 4 3 |
| Cypothrin 7.5% plus dimethoate 7.5% | 51 71 |
| Cypothrin 7.5% plus dibrom 7.5% | 97 89 |
| Cypothrin 7.5% plus chlorfenvinphos 7.5% | 1 0 |
| Control - None | 1 |

EXAMPLE 7

Preparation of a one piece matrix animal ear tag by extrusion onto polyester cloth Two dry blends are prepared by the procedure of Example 1 containing, on a weight basis, 100 parts PVC, 18.88 parts epoxidized soybean oil, 0.54 parts stearic acid, 0.65 parts trinonylphosphate, 1.96 parts Ca/Zn stearate, 0.44 parts HYP212, 0.76 parts HYP211, 2.0 parts HW132, 0.65 parts UIV stabilizer, 36.0 parts piperonylbutoxide, 19 parts flucythrinate; one with 18 parts Benzylbutylphthalate (BBP), and the other with 18 parts acetyltributylcitrate (ATBC). Each of these dry blends are coated onto a fabric mesh matrix by coextruding the melt through a profile die onto the matrix. The resulting impregnated matrix is cut into the shape of a standard one piece animal ear tag weighing approximately 8.5 grams.

These insecticidal ear tags are hung in a chamber covered with mesh cloth to keep the flies confined in the 12×17"×9" space. Each chamber contains a cup of water and a supply of sugar and powdered milk.

At the start of the test, ~100 three to five day old house flies are placed in each chamber. The chambers are kept in a room with the temperature at 82° F. The flies are observed daily (except Saturday and Sunday) and mortality is recorded. At the termination of the study, the chambers are placed in a freezer overnight to kill the remaining flies, which are counted. The percent mortality is calculated based on the number of flies that die during the observation and the number of flies counted at the end of the study.

The results of these experiments which are summarized in Table VII below demonstrate the effectiveness of the insecticidal matrix ear tags of the invention against both a pyrethoid resistant and normal strain of house flies.

TABLE VII

| | 7 Day Fly Morality % | |
|---|---|---|
| Plasticizer | Pyrethoid Resistant Strain | Normal |
| BBP | 5 | 67 |
| ATBC | 82 | 99 |

What is claimed is:

1. An animal ear tag comprising a first component which is capable of being attached to the ear of an animal, a second component comprising on a weight basis about 44.0% to 71% of a polyvinylchloride or other thermoplastic; about 0.0% to 4.0% of a processing stabilizer; about 0.2% to 10.0% of a lubricant; about 0.3% to 0.5% of a chelating agent; about 1% to 2.5% of a heat processing stabilizer: about 0% to 5.0% of a flow agent; about 0% to 35.0% of insecticidal synergists and migration accelerators; about 5.0% to 25.0 % of a plasticizer or mixture of plasticizers; about 1% to 30% of an insecticide or mixture of insecticides, and a means for connecting the two components wherein the components are joined together to provide for a degree of motion between the first and second components.

2. An ear tag according to claim 1, wherein the second component is fabricated on a matrix of a natural or synthetic cloth or fiber mesh, wire mesh or a solid.

3. An ear tag according to claim 2, wherein the second component is fabricated in sections which are comprised of the same or different insecticides.

4. An ear tag according to claim 1, wherein the insecticide is selected from a group consisting of pyrethoids, organophosphates, carbamates and mixtures thereof 5. An ear tag according to claim 4, wherein the pyrethroid insecticide is flucythrinate, fenvalerate, cypermethrin, permethrin, cypothrin, deltamethrin, fluvalinate, cyhalothrin, or (Z)-trans-α-cyano-m-phenoxybenzyl, 3-(β-cyanostyryl)-2,2-dimethylcyclopropanecarboxylate.

6. An ear tag according to claim 4 wherein the organophosphate insecticide is dimethoate, dibrom or chlorfenvinphos.

7. An animal ear tag comprising one mesh matrix component of a natural or synthetic cloth or fiber or wire fabricated with a composition comprising on a weight basis about 44.0% to 71% of a polyvinylchloride or other thermoplastic; about 0.0% to 4.0% of a processing stabilizer; about 0.2% to 10.0% of a lubricant; about 0.3% to 0.5% of a chelating agent; about 1% to 2.5% of a heat processing stabilizer; about 0% to 5.0% of a flow agent; about 0% to 35.0% of insecticidal synergists and migration accelerators; about 5.0% to 25.0% of a plasticizer or mixtures of plasticizers; about 1% to 30% of an insecticide or mixture of insecticides.

8. An ear tag according to claim 7, wherein the insecticide is selected from a group consisting of pyrethoids, organophosphates, carbamates and mixtures thereof.

9. An ear tag according to claim 8, wherein the pyrethroid insecticide is flucythrinate, fenvalerate, cypermethrin, permethrin, cypothrin, deltamethrin, fluvalinate, cyhalothrin, or (Z)-trans-α-cyano-m-phenoxybenzyl, 3-(β-cyanostyryl)-2,2-dimethylcyclopropanecarboxylate.

10. An animal ear tag according to claim 8, wherein the organophosphate insecticide is dimethoate, dibrom or chlorfenvinphos.

11. An ear tag according to claim 7, wherein the plasticizer is a citrate ester.

12. An ear tag according to claim 7, wherein the component is fabricated by extrusion or coextrusion.

13. A method for controlling insects in a localized environement, said method comprising: contacting an animal with an ear tag comprising a first component which is capable of being attached to the ear of the animal, a second component comprising on a weight basis about 44.0% to 71% of a polyvinylchloride or other thermoplastic; about 0.0% to 4.0% of a processing stabilizer; about 0.2% to 10.0% of a lubricant; about 0.3% to 0.5% of a chelating agent; about 1% to 2.5% of a heat processing stabilizer; about 0% to 5.0% of a flow agent; about 0% to 35.0% of insecticidal synergists and migration accelerators; about 5.0% to b 25.0% of a plasticizer or mixtures of plasticizers; about 1% to 30% of an insecticide or mixture of insecticides, and a means for connecting the two components, wherein the components are joined together to provide for a degree of motion between the first and second components.

* * * * *